United States Patent
Al-Gouhi et al.

(10) Patent No.: US 10,613,053 B2
(45) Date of Patent: Apr. 7, 2020

(54) ELECTROPHORESIS ANALYSIS TO IDENTIFY TRACERS IN PRODUCED WATER AT A WELL HEAD

(71) Applicant: Saudi Arabian Oil Company, Dhahran (SA)

(72) Inventors: Alwaleed A. Al-Gouhi, Dhahran (SA); Mohamed Nabil Noui-Mehidi, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 324 days.

(21) Appl. No.: 15/793,144

(22) Filed: Oct. 25, 2017

(65) Prior Publication Data
US 2019/0120791 A1 Apr. 25, 2019

(51) Int. Cl.
*G01N 27/447* (2006.01)
*E21B 43/12* (2006.01)
(Continued)

(52) U.S. Cl.
CPC ....... *G01N 27/44747* (2013.01); *E21B 43/12* (2013.01); *E21B 43/14* (2013.01);
(Continued)

(58) Field of Classification Search
CPC ...... E21B 43/12; E21B 43/14; E21B 47/1015; E21B 47/1025; G01N 27/44791;
(Continued)

(56) References Cited

U.S. PATENT DOCUMENTS 6,645,769 B2  11/2003  Tayebi et al.
8,322,414 B2  12/2012  Al-Gouhi et al.
(Continued)

FOREIGN PATENT DOCUMENTS

WO  2014/014587 A2  1/2014
WO  2015/023917 A1  2/2015

*Primary Examiner* — Gurpreet Kaur
(74) *Attorney, Agent, or Firm* — Abelman, Frayne & Schwab

(57) ABSTRACT

An automated method and system for identifying one or more chemical tracers present in a sample drawn downstream from the well head from a produced hydrocarbon oil/water stream in a pipeline from a downhole well completion, the one or more chemical tracers having originally been applied to the outer surface of one or more lengths of tubing placed at known locations in the assembly of the downhole well completion, the chemical identification of each of the tracers and the location of each of the tracers having been retrievably recorded for the well completion in the form of a relational database, by in situ testing of a portion of the aqueous layer of the sample following settling by means of an electrophoresis analysis system that includes a microfluidic chip and an electronic data information collection unit and signal communication means for transmitting conditioned data from the electronic data information collection unit to the central control station for comparison with, and identification of data associated with the chemical tracers and the location of the chemical tracers in the well completion from the relational database, and a user display device for displaying the results of the data comparison and identification so that appropriate remedial action to reduce the volume of produced water in the hydrocarbon stream can be taken.

22 Claims, 4 Drawing Sheets

(51) Int. Cl.
*E21B 43/14* (2006.01)
*E21B 47/10* (2012.01)
*G01N 27/00* (2006.01)
*G01N 33/24* (2006.01)
*G01N 1/10* (2006.01)
*G01N 1/20* (2006.01)

(52) U.S. Cl.
CPC ......... *E21B 47/1015* (2013.01); *G01N 27/00* (2013.01); *G01N 27/44726* (2013.01); *G01N 27/44769* (2013.01); *G01N 27/44782* (2013.01); *G01N 33/246* (2013.01); *G01N 27/44743* (2013.01); *G01N 27/44791* (2013.01); *G01N 2001/105* (2013.01); *G01N 2001/205* (2013.01)

(58) Field of Classification Search
CPC ....... G01N 27/44743; G01N 27/44782; G01N 27/44726; G01N 27/44769; G01N 2001/205; G01N 2001/105
See application file for complete search history.

(56) References Cited

U.S. PATENT DOCUMENTS

| | | | |
|---|---|---|---|
| 8,596,354 B2 * | 12/2013 | Hartshorne | E21B 47/1015 166/250.12 |
| 9,976,417 B2 * | 5/2018 | Mahavadi | E21B 49/08 |
| 2015/0047979 A1 * | 2/2015 | Mahavadi | E21B 49/087 204/453 |
| 2015/0308224 A1 | 10/2015 | Dyer | |
| 2017/0045476 A1 | 2/2017 | Mahavadi et al. | |

* cited by examiner

ELECTROPHORESIS ANALYSIS TO IDENTIFY TRACERS IN PRODUCED WATER AT A WELL HEAD

BACKGROUND OF THE INVENTION

Field of the Invention

This invention relates to a system and method for identifying one or more locations of water breakthrough in horizontal sections of a multi-zone subterranean hydrocarbon-producing well by analysis to identify tracers in produced fluids at the well head on the earth's surface.

Description of Related Art

A principal objective of advanced well completions is to provide flow control over inflow areas among the different horizontal sections of the well bore. This flow control is heavily dependent on the reliability of the open-hole packers that are installed to form isolated compartments defined by the production tubing and the surrounding reservoir rock wall that is the well bore. The purpose of installing the open-hole packers is to isolate the sections of the production tubing that are perforated to receive the inflow of produced oil from the intervening regions through which the remainder of the "blank" or non-perforated tubing passes. As used herein, the term blank tubing means production tubing that is not perforated and does not constitute an inflow control device (ICD) for admitting hydrocarbon fluids into the tubing for production to the earth's surface.

The surface of the rock in the well bore can be irregular, even in carbonate formations. Such irregularities can interfere with the ability to form a reliable fluid-tight seal using the open-hole packer. The ability to confirm at the Earth's surface that the open-hole packers are completely sealing off the compartments as intended and that the objectives of the advance well completion have been achieved is of particular importance from the standpoint of well management, and because of the high cost of installing the open-hole packers.

The use of various types of tracers and tracer compositions in conjunction with well completions is known in the art. There is sufficient turbulence created in the produced fluids passing from the downhole well completion to the well head to ensure that any tracer chemicals are well mixed and homogeneously present in the produced oil/water stream when sampled downstream of the well head. Several of the patents discussed below utilize tracers to identify the source of fluids produced from the reservoir and to identify specific locations or zones along the bore hole where the fluid(s) entered the bore hole.

One limited solution to the problem of identifying the general area that is the source of produced water has been to coat the interior of at least a portion of the pipe in the toe section of the horizontal tubing with a water-soluble phosphorescent composition. Water entering that compartment will solubilize the tracer. If tests of water produced with the oil at the surface show presence of the tracer compound, it will be known that at least the toe compartment was producing water. In the event of a failure of the packer adjacent the ICD, water containing the tracer will infiltrate the producing compartment and be produced with oil at the surface. Thus, the surface test will be inconclusive as to the actual location(s) of the water incursion(s).

The use of soluble chemical tracer compounds and compositions in a well completion in accordance with the prior art will be described with reference to FIG. 1. As illustrated, the completion 100 includes a vertical well bore section 10 extending from the earth's surface 9 and containing production tubing 12 and casing 14, with a production packer 16 that seals the annulus between the casing and tubing. It will be understood by one of ordinary skill in the art that the length of the vertical section 10 can be many thousands of feet. The horizontal section 20 of the open well bore is also of indeterminate length and is defined by the curved transitional heel portion 22 and the completion end, or toe, 24. The casing 14 terminates at region 15 which defines the beginning of the open hole portion of the well. In the illustration of FIG. 1, the horizontal length of tubing is identified as element 40 and is fitted with an input control device (ICD) 48 in the toe 24 of the open bore hole. Additional ICDs 48A, 48B and 48C are positioned along the horizontal tubing string 40 in a series of spaced-apart hydrocarbon production zones. These input control devices 48A-48C are isolated by open-hole packers 50A, 50B, 50C, 50D, 50E and the production packer 16, thereby forming production flowing compartments 1, 2, 3 and 4. This configuration of completion can be used where the horizontal well bore 20 passes through one or more additional hydrocarbon-producing zones that correspond generally to the flowing compartments. These additional production zones can be located some distance from the toe end 24 of the horizontal well bore where ICD 48 is located.

A method and system of applying one or more water-soluble tracer compositions and oil-soluble tracer compositions as coatings on at least a portion of the exterior surface of a section of blank production tubing that is positioned between one or more open-hole packers that define a non-flowing compartment that is proximate an inflow control device or devices in a horizontal well section is described in U.S. Pat. No. 8,322,414, the disclosure of which is incorporated herein by reference.

The surfaces of tubing sections 42 in non-flowing compartments adjacent to the flowing compartments are coated with water-soluble and oil-soluble marker compositions, each of which have distinctive and distinguishable characteristics that can be individually identified at the surface test station 84. Also shown in FIG. 1 is sampling point 81 located at the well head 80 that includes valve 82.

With continuing reference to the well completion of FIG. 1, the method of determining the seal effectiveness of one or more compartments includes the steps of coating the exterior surface of the tubing in the non-flowing compartment A with water-soluble and oil-soluble tracers 60A; coating the exterior surface of the tubing in the non-flowing compartment B with water-soluble and oil-soluble tracers 60B; coating the exterior surface of the tubing in the non-flowing compartment C with water-soluble and oil-soluble tracers 60C, where tracers A, tracers B and tracers C are, respectively, three different water-soluble and oil-soluble tracers that can readily be recognized and distinguished separately when produced and sampled at the well head and the samples are subjected to testing of the type known to the art.

Assuming that the open-hole packer 50A fails and 50B is holding, tracers 60C will be produced with the reservoir fluids entering the flowing compartment 3. Tracers 60C will be detected with the produced reservoir fluids at the well head. As a result, the samples tested will show that the packer for the non-flowing compartment C is not functioning. In this case, the flowing compartment 4 and the non-flowing compartment C are considered as one compartment. However, the effect of the open-hole packer 50B will be negligible without the sealing of 50A. Therefore, flowing compartment 4, non-flowing compartment C and the flowing compartment 3 are considered as one compartment.

In the case where the open-hole packer 50B fails and 50A is holding, tracers 60C will be produced with the reservoir fluids entering the flowing compartment 3, and tracers 60C will be detected with the produced reservoir fluids at well head. As a result, it will be shown by the test results of 84 that the non-flowing compartment C is not functioning. In this case, the flowing compartment 3 and the non-flowing compartment C are considered as one compartment. However, the effect of the open-hole packer 50A will be negligible without the sealing of 50B. Therefore, flowing compartment 4, non-flowing compartment C and the flowing compartment 3 are considered as one compartment. As will be understood from the illustration of FIG. 1, the failure of any one of the open-hole packers will result in the passage of any reservoir fluids present in a non-flowing compartment into the compartment adjacent to the failed open-hole packer.

If the water-soluble tracer is detected at the surface in a produced oil-and-water mixture, it can be concluded that an open-hole packer is leaking water into the adjacent oil-producing section. If the oil-soluble tracer is detected at the surface, it can be concluded that the open-hole packer adjacent an ICD has failed and oil has contacted the coating.

The tracer compositions of the '414 patent are in the form of a surface coating composition containing water-soluble and preferably water-soluble and oil-soluble tracer compounds that are applied to the exterior surface of a section of pipe or production tubing, i.e., marker tubing, at the earth surface prior to its being lowered for positioning in the well bore. The water-soluble tracer compound is soluble in produced formation fresh or salt water and/or such injection water that is pumped into the formation to enhance production. Similarly, the oil-soluble tracer compounds are soluble in the produced hydrocarbon fluids. In completions where multiple compartments are to be monitored, a different and distinguishable tracer compound is applied to each compartmentalized section of marker tubing.

The purpose of the tracers of the '414 patent are to identify the lack of effectiveness of open-hole packers that are used to compartmentalize portions of the production tubing string adjacent the inflow control device(s) (ICDs) in the horizontal well bore. In the event that one or more tracer compounds are detected at the surface in the produced hydrocarbon fluid, it provides an indication that the portions containing the tracer coating have not been completely isolated, or compartmentalized, and water is being passed to the ICD.

The effectuation of each of the prior art methods described above are dependent on reliable methods for first determining whether the produced fluids sampled at the well head contain any of the one or more tracer compositions and, if so, the specific composition and concentration of the one or more compositions. Water cut sensors placed at the well head can alert well managers to the presence of water in the produced hydrocarbon stream. A sample of the produced water/hydrocarbon stream is drawn from a valved sampling point downstream of the well head. The sample must then be delivered to a lab for analysis and identification of the specific tracers present based on analyses to identify their characteristics which can include radioisotopes, and biological compounds, as well as chemical compounds and compositions. A variety of such tracers are identified in U.S. Pat. No. 6,645,769.

Depending upon the location of the sampling point, a substantial amount of time may pass from the initial water sensor alarm and the forwarding of the lab report identifying the specific tracers to the well manager for action. During the period of delay, produced water is sent to the GOSP.

Electrophoresis is a technique known in the art for separating molecules based on size and charge based on electrokinesis. Electrophoresis of positively charged particles is called cataphoresis, while electrophoresis of negatively charged particles is called anaphoresis. During electrophoresis processing, a negative charge is applied to a system. Depending on the molecules' size and charge, the molecules will move in different directions and/or at different speeds, providing the desired separation.

From the above, it will be understood that there is a need in the art for a reliable and efficient system and method for detecting the presence of tracers and, if tracers are found to be present, analyzing and identifying the tracer compositions present in produced well fluids at the earth's surface in real time.

A further problem addressed is how to provide a direct analytical method and system for the identification of specific chemical tracers in real time and in proximity to the well head downstream sampling point and communicating the information to the well management engineers for appropriate remedial action to promptly reduce the water cut, or amount of water being produced with the hydrocarbons from the well.

Another problem addressed by the present disclosure is providing an electrophoresis system that is compact, reliable and easy to maintain, and that can be placed in proximity to the well head sampling point in the oil field environment and operated remotely.

Another problem is providing an automated analytical system for identifying specific tracer compositions that can be operated in remote locations and that has the capability to promptly transmit the test results electronically to a central control station for management of the oil field and reduction of the amount of water in the produced fluids.

Also addressed is providing an automated system in a remote location that will interrupt the sampling protocol when one or more essential consumable supplies have been depleted and service is required by technical personnel.

SUMMARY OF THE INVENTION

The above problems are resolved and other advantages are achieved by the method and system of the present disclosure which employs an electrochemical analytical system that incorporates electrophoresis to identify one or more chemical tracers in a sample of produced water from a well completion taken from a sampling point proximate to, and downstream from the well head at the earth's surface.

In an embodiment, one or more water soluble and oil soluble tracer chemicals are applied to the exterior of one or more zones in a downhole well completion. A water-cut sensor located downstream of the well head is configured to detect a predetermined increase in water produced in the produced fluids and generates an alarm signal that is transmitted to a central control station. In response to the alarm, an automated sampling valve, which is preferably a ball valve, is actuated to withdraw a predetermined amount of the pressurized produced oil/water stream from a sampling point on the pipeline downstream of the water-cut sensor. The automated sampling valve can be actuated by personnel at the central control station or, optionally, the alarm signal is transmitted directly to actuate the valve which opens to withdraw the sample. In either event, the pressurized sample from the pipeline is passed via a sampling conduit to a nearby vented sample collection vessel.

The oil/water sample admitted occupies approximately one-half of the volume of the sample collection vessel. The sample collection vessel is equipped with a drainage port and mechanism to discharge any liquid remaining after the analysis has been completed. The sample collection vessel can also be provided with an overflow discharge port and an overfill sensor and shut-off switch that is in communication with the sampling valve to stop the flow from the pipeline.

After the automated sampling valve is closed, the oil/water sample is allowed to settle for a predetermined period time that is sufficient for the oil and water to substantially separate due to gravity. Based on their density, the oil layer rises to the top and an aqueous layer forms at the bottom of the collection vessel. A predetermined portion of the aqueous layer is withdrawn via a flexible aqueous sample transfer tube that is in fluid communication with the lower portion of the sample collection and settling vessel and preferably passed to a secondary sample retention vessel located in a protective housing where it is protected from potentially adverse/environmental conditions that may be prevalent at the remote well site.

The sample passes via a flexible aqueous sample transfer tube that is preferably a polymeric material that is inert and resistant to the chemical tracers and to the buffer composition. The aqueous sample is then passed from the secondary sample retention vessel to the inlet port of a peristaltic pump which is operated to deliver the aqueous sample at a predetermined rate and pressure to the inlet of an analytical electrophoresis system [ES]. In an embodiment, ES is mounted in a micro-fluidic chip that has an inlet port that serves as the sample reservoir and an entry port for the buffer electrolyte that is used in the electrophoresis process. After the sample is introduced into the capillary tube, or the micro-fluidic chip device, a high voltage differential is applied between the inlet port of the electrolyte and the exit of the capillary tube or the micro-channel.

In a preferred embodiment, a microprocessor and controller are programmed to initiate the sequence of operations that begins with the actuation of the automated sampling valve based on localized prevailing parameters, e.g., of the temperature and pressure of the oil/water stream in the pipeline at the sampling point downstream of the well head. The data corresponding to these and other parameters is obtained by conventional sensors that routinely transmit such data to the well or field management central control station for monitoring.

The controller functions as follows: (1) to open and then close the sampling valve after a predetermined period of time to provide the desired volume of sample to the collection vessel; (2) to maintain the sample for a predetermined period of time during which the water substantially separates from the oil; (3) to actuate the peristaltic pump for a predetermined period of time to pressurize the electrophoretic system [ES] with the aqueous sample; (4) to stop the peristaltic pump in response to signals from one or more pressure and/or flow sensors associated with the ES; (5) to actuate the ES by applying a predetermined voltage potential to initiate the separation of chemical tracer compounds in the aqueous sample; (6) to modify the operating parameters of the ES in response to signals transmitted by ES chemical sensors upon detection and identification of chemical tracer compounds; (7) to modify or turn off the voltage supplied to the ES; and (8) to open a buffer solution flushing valve adjacent the automated sampling valve to admit a pressurized flushing solution into the sampling conduit, to open a waste discharge valve on the sample collection vessel in order to remove the separated oil and any remaining water, and to flush the aqueous sample from the flexible aqueous sample transfer tube and the ES.

The operation of the electrophoresis system of the present disclosure is based on an electro-kinetic principle that is known in the art. The electrophoresis system separates chemical species present in the water-based sample by mass and charge. The electrophoretic signature(s) of the compounds in the aqueous sample are compared to an existing electronic database that includes data on each of the chemical tracers applied to pipes in the well completion from which the produced oil/water stream was sampled.

The electrophoresis system of the present disclosure is advantageously a micro-fluidic chip having inlets to receive the aqueous sample and an aqueous buffer solution. Suitable buffer solutions include, for example, acetic acid, boric acid, glycine, phosphoric acid, taurine, tricine and citric acid.

A potential difference is applied across the micro-fluidic chip via a high voltage source. Potential difference values can range from 1 kV to 5 kV. The required voltage can advantageously be provided by conventional circuitry connected to a storage battery that is charged by a solar power source located at the sampling/test site. One or more storage batteries and their associated control circuits are preferably maintained in a protective housing, which can be the same or separate from the ES.

A chemical conductivity sensor is located proximate the exit of the micro-fluidic chip, is configured to detect the presence of chemical species based on the conductivity and mobility of the molecule(s) present and transmits data for eventual display to the user via a GUI that identifies the molecule or molecules present in the aqueous sample by comparison to data in a library or database stored in an electronic memory unit that is most conveniently maintained at the central control station or other secure remote location. By applying systems and programs known to those of ordinary skill in the art, this method can be employed to provide both qualitative and quantitative values for the amount of the species present in the water sample collected, and by this method complete the analysis of the clerical tracers in the produced fluids in realtime.

From the preceeding description, it will be understood that the method and system of the present disclosure is configured to access an existing electronic database that contains (1) stored information that is sufficient to identify all of the unique tracers that are applied to the exterior of the marker pipes that are used in the multi-zone subterranean well completion, and (2) the precise location of each of the marker pipes to which the unique tracer has been applied. This comparative database is established and maintained in accordance with a well completion design that is created and updated as required by the well or oil field management engineer or group. As will also be understood by one of ordinary skill in the art, conventional elements such as sensors, flow valves, drain valves, pumps, recording gauges, overflow and waste lines, control devices and electrical wiring are not shown in these simplified schematic drawings for convenience and to facilitate the explanation and the understanding of the principal features and operational characteristics of the respective embodiments of this disclosure.

BRIEF DESCRIPTION OF THE DRAWINGS

The system and method of this disclosure will be described in more detail below and with reference to the attached figures in which the same numbers are used for the same or similar elements, and where.

DETAILED DESCRIPTION OF THE INVENTION

Figure 1:
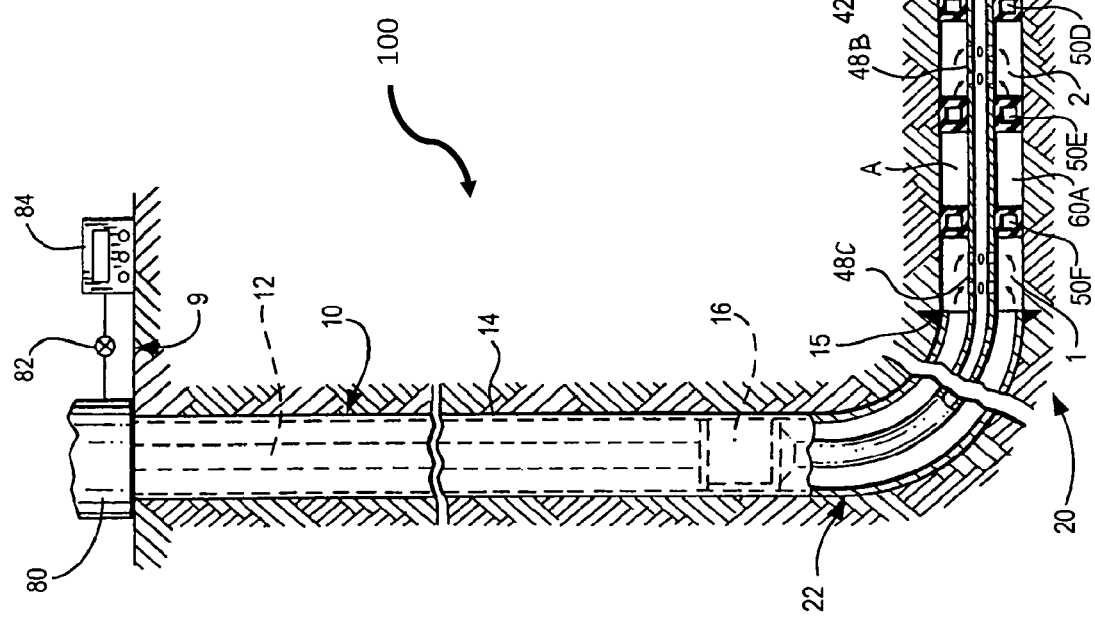
FIG. 1 is a schematic diagram of a well completion of the prior art.
Figure 2:
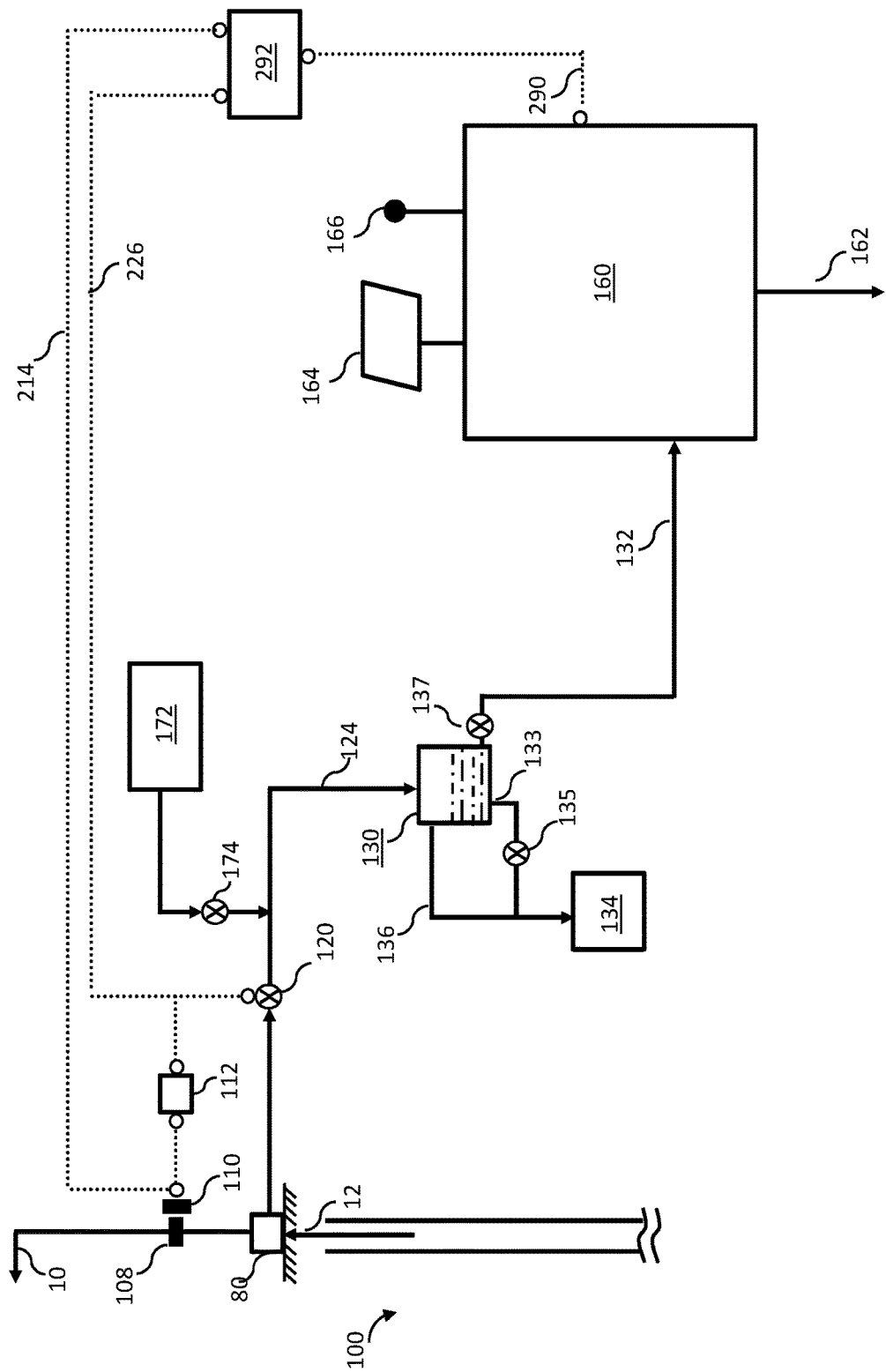
FIG. 2 is a flow diagram of the electrophoresis analysis system of the present disclosure.

Referring now to FIG. 2, in accordance with the method and system of the present disclosure, produced fluids from well completion 100 contact water-cut sensor 110 downstream of well head 80. Due to the turbulence in downstream well completion 100, any dissolved chemical tracer compounds present are thoroughly mixed in the produced fluids. If the water-cut exceeds a predetermined value, a signal is sent from water-cut sensor 110 via water-cut sensor signal line 214 to a central control station 292, which can be a supervisory control and data acquisition (SCADA) unit of a type known in the art. In accordance with an operating protocol, a signal is sent to open automated sampling valve 120 via sampling valve signal line 226 automatically or, alternatively, by personnel monitoring the system. It will be understood that signals and data transmission can advantageously be transmitted wirelessly to and from remote locations using dedicated secure transponders and/or the internet.

In an embodiment in which the system is automated, the signal from water-cut sensor 110 can be sent via water-cut sensor signal line 214 to a microprocessor 112 that is programmed to transmit a signal via control valve signal line 226 to open the sampling valve and also to alert personnel in the control station 292 of the initiation of the sampling step.

Automated sampling valve 120 is programmed to open for a predetermined period of time to admit a desired volume of the pressurized oil/water sample via sampling conduit 124 from the sampling point 108 in transmission pipeline 12 and into a sample collection vessel 130, and then to close. The sample collection vessel is preferably filled to approximately one-half of its capacity to avoid overfilling. The sample collection vessel can include an overflow port and conduit 132 to a waste storage vessel 134, an overfill sensor and transmitter operationally connected to automated sampling valve 120, and a drainage port 133 and valve 135 for discharge of excess water, oil and buffer flushing solution to waste storage vessel 134 after the testing is complete.

The oil/water sample is allowed to settle in vessel 130 for a predetermined period of time, and separation of the oil and water occurs due to differences in densities, with the water gravitating to the bottom of sealed container 130 as aqueous layer 132. After the predetermined settling time, valve 137 is opened to permit a portion of the aqueous layer 132 to exit collection vessel 130 via an outlet pipe or tube 131 proximate the bottom of collection vessel 130.

In a preferred embodiment, the ES, microprocessor and controller, data transmitter/receiver, electrical storage battery, and associated apparatus are contained in a protective housing to shield it from local environmental conditions. The housing can also provide support for a solar energy collector and an exterior antenna for the transmission and receipt of signals.

Figure 3:
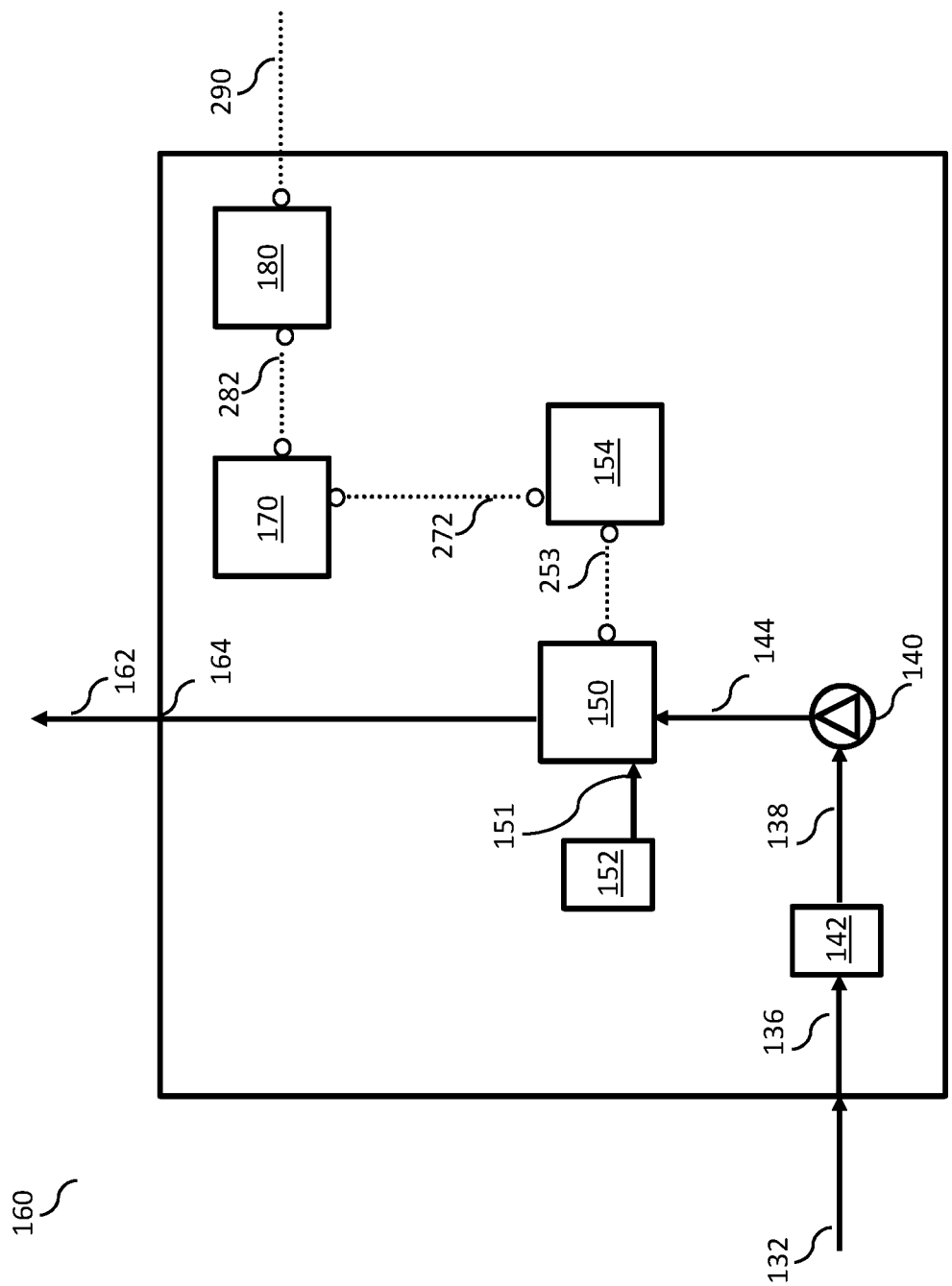
FIG. 3 is a flow diagram of the chemical analysis housing of the present disclosure.

Referring to FIG. 3, the water sample 132 passes to the protective housing 160 and into aqueous sample retention vessel 142. A relatively small amount of the aqueous sample 138 that is required for the chemical tracer analysis passes from the sample retention vessel 142 to the peristaltic pump 140 and is delivered under pressure to the electrophoresis analysis micro-fluidic chip 150. A buffer solution is passed via buffer conduit 151 from ES buffer storage vessel 152 to the micro-fluidic chip 150 where it mixes with the aqueous layer sample 144. The voltage applied to this mixture will lead to the phoretic separation of the individual species present in the aqueous samples introduced into the ES.

The aqueous sample is analyzed in micro-fluidic chip 150 to produce a chemical identification signal. The signal produced in micro-fluidic chip 150 travels via signal line 253 to the micro-fluidic chip electronic control and data acquisition unit 154. Data is transmitted from the micro-fluidic chip electronic control and acquisition unit 154 and is sent via signal line 272 to the electronic data information collection unit 170 where it is stored. The data can be stored on a disk or any other convenient form of memory. Data from the electronic data information collection unit 170 is transmitted via signal line 282 to communication system 180 to condition the data before sending it via 290 to the central control station 292 where it can be displayed on a GUI at that location and/or for comparison with the stored data for the tracers employed in the well completion to identify the location of the water break through.

Figure 4:
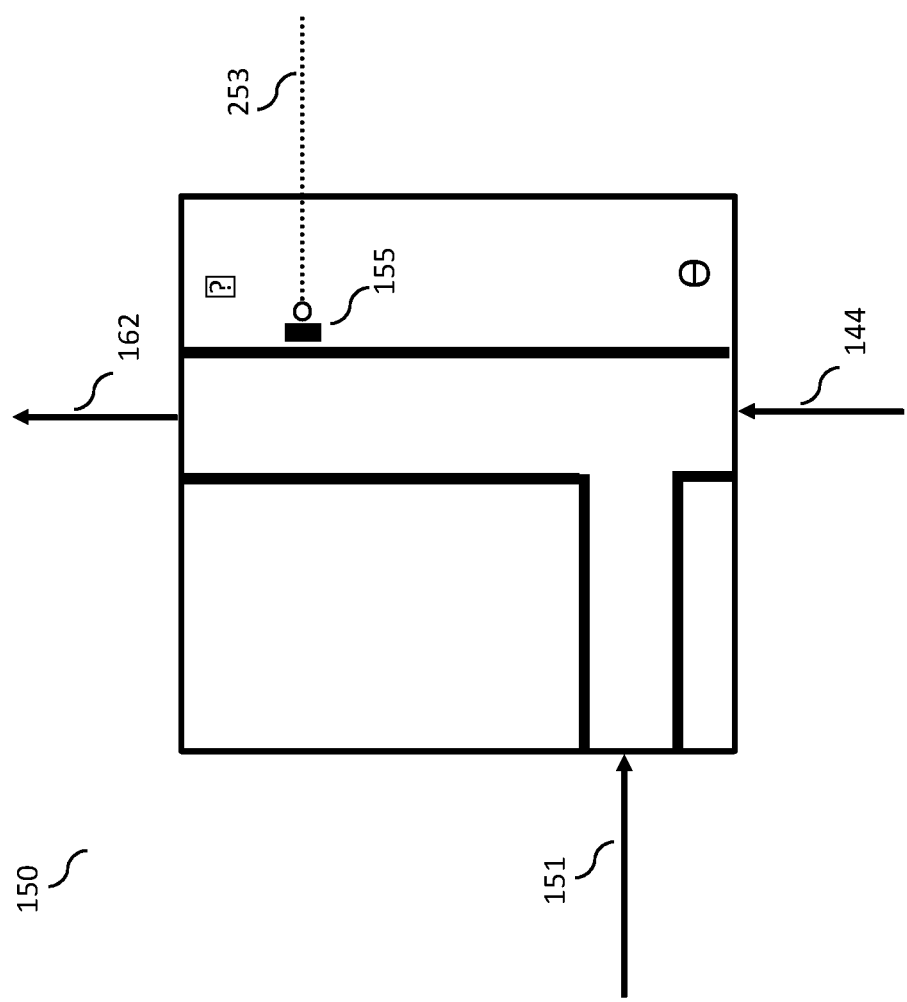
FIG. 4 is a flow diagram of the micro-fluidic chip of the present disclosure.

Referring now to the enlarged simplified schematic illustration of FIG. 4, aqueous layer sample from conduit 144 and buffer conduit 151 enter micro-fluidic chip 150 where they are mixed. A potential difference is applied across the chip at a voltage in the range of from 1 kV to 5 kV. The required voltage for micro-fluidic chip 150 can be provided by appropriate circuitry connected to a storage battery that is charged by a solar power source 164 located at the sampling/test site.

In an embodiment, the potential difference is applied so that the end of the chip at which the aqueous sample was admitted is electro-negative and the negatively charged molecules travel toward the positively charged end of the chip. Molecules that have a higher negative charge and a lower molecular weight will travel more quickly through the chip. Electrophoretic sensor 155 is placed proximate the positively charged end of chip 150 for detection of chemical species present. Data from sensor 155 is transmitted via line 253 to the electronic control and data acquisition unit 154. It will be understood by those skilled in the art that the electronic signals can be transmitted via wire lines, or wirelessly via antenna 166 from remote locations.

From the above description, it will be understood that this disclosure broadly comprehends a system for identifying one or more chemical tracers present in a produced hydrocarbon oil/water stream in a pipeline from a downhole well completion, the one or more chemical tracers having originally been applied to the outer surface of one or more lengths of tubing placed at known locations in the assembly of the downhole well completion, the chemical identification of each of the tracers and the location of each of the tracers having been retrievably recorded for the well completion in the form of a relational database, the system comprising:

a. a water-cut sensor for detecting water present in the oil/water stream flowing in the pipeline and an associated alarm for transmitting a signal to a central control station, and/or to a microprocessor controller;

b. an automated sampling valve in communication with the water-cut sensor alarm and in electronic communication with the central control station and/or the microprocessor controller, the sample valve configured to open for a predetermined period of time in response to a signal to pass a predetermined volume of a sample from the produced oil/water stream through a sampling point in the pipeline;
c. a sample collection vessel in fluid communication with the sampling valve for receiving the sample of oil/water from step (b), the collection vessel comprising an outlet port proximate the bottom of the vessel for passage of a portion of the aqueous layer of the sample following settling; and
d. a resilient polymeric sample transfer tube disposed to receive a portion of the settled aqueous sample, the transfer tube being in fluid communication with the inlet of a peristaltic pump, the peristaltic pump configured and controlled to transfer from an outlet port a predetermined volume of the aqueous sample under pressure to an electrophoresis analysis micro-fluidic chip, where the micro-fluidic chip comprises:
an inlet for admitting the aqueous sample,
an inlet for admitting a liquid buffer solution,
electrical connections for receiving a controlled voltage, and
an electrophoresis sensor;
e. a micro-fluidic chip electronic control and acquisition unit in electronic communication with the electrophoresis sensor;
f. an electronic data information collection unit in electronic communication with the micro-fluidic chip electronic control and acquisition unit;
g. signal communication means for transmitting conditioned data from the electronic data information collection unit to the central control station for comparison with, and identification of data associated with the chemical tracers and the location of the chemical tracers in the well completion from the relational database; and
h. a user display device for displaying the results of the data comparison and identification of step (g).

After the analysis is completed, in an embodiment, the micro-fluidic chip 150 is flushed with the buffer solution from storage vessel 152 to remove the remains of the processed sample in preparation of the ES for the introduction of the next sample. As will be described in more detail below, the whole system can be flushed with buffer from buffer vessel 172 when buffer valve 174 is opened to remove unused sample and other unwanted components via a waste discharge stream 162. Customary sampling protocols are employed to flush the pipeline sampling tube to flush any of the oil/water mixture remaining from the prior sampling.

At the conclusion of the sampling, analysis, data collection and data transmission, the apparatus of the entire system must be prepared for a subsequent sampling sequence, i.e., after the well engineers have reduced the water-cut to an acceptable level. This preparation of the system includes the flushing of all of the conduits and vessels contacted by the prior sample, and of the ES. This is accomplished by providing a flushing buffer solution storage vessel having a predetermined capacity that will be sufficient to flush the entire system after a predetermined number of sampling events. The buffer solution must be pressurized to assure that it passes from the storage vessel with sufficient force to remove the oil/water mixture from the sampling conduit and the sample collection and settling vessel. In an embodiment where the buffer solution will also be supplied from the vessel to the ES, a detergent or other liquid cleaning agent can be injected into the flushing buffer solution downstream of the storage vessel. Alternatively, the detergent can be added to the flushing buffer solution in the storage vessel and passed as a pressurized stream for a predetermined period of time to clear to conduits and vessels downstream from the automated sampling valve.

It will also be understood that upon the subsequent introduction of an oil/water sample from the pipeline, the conduits and vessels will have to be purged of the buffer solution, e.g., by opening a discharge port valve in the bottom of the sample collection vessel for a predetermined period of time and preferably passing the mixture to a waste storage vessel for eventual disposal. Following settling of the mixture, the aqueous sample is used to flush any remaining traces of the flushing buffer solution from the remaining conduits and vessels upstream of the ES.

It will also be understood from the above description and drawings that the present method and system can be applied for the identification of other types of tracers known in the prior art. As will also be apparent from the above description that the present method and system can be adapted to remove a portion of the hydrocarbon layer from the sample collection vessel after the oil/water sample has settled for identification of oil-soluble tracer compounds.

The invention has been described in detail above and illustrated in the attached drawings and other embodiments and modifications will be apparent to those of ordinary skill in the art from this description. The scope of the invention is to be determined by the claims that follow.

The invention claimed is:

1. A method of identifying one or more chemical tracers present in a produced hydrocarbon oil/water stream flowing in a pipeline from a downhole well completion, where the downhole well completion includes a well head, and the one or more chemical tracers, each having a predetermined chemical identification, having originally been applied to an outer surface of one or more lengths of tubing placed at known locations during the assembly of the downhole well completion, the chemical identification of each of the chemical tracers and the location of each of the tracers having been previously recorded and retrievably stored for the downhole well completion as a relational database, the method comprising:
a. passing the oil/water stream in contact with a water-cut sensor and transmitting an alarm signal from the water-cut sensor in response to the presence of water in the oil/water stream in an amount greater than a predetermined value;
b. remotely actuating an automated sampling valve at a sampling point in fluid communication with the oil/water stream in the pipeline downstream of the well head in response to the alarm signal from the water-cut sensor, and admitting a predetermined volume of an oil/water sample from the pipeline into a sample collection vessel;
c. allowing the oil/water sample to settle for a time sufficient to form an oil layer and an aqueous layer in the sample collection vessel;
d. transferring a portion of the aqueous layer under pressure into a micro-fluidic chip configured for electrophoretic analysis and mixing the aqueous layer with a buffer solution to produce a buffered aqueous solution;
e. applying an electro potential difference across the micro-fluidic chip to effectuate a migration of molecules comprising the one or more tracer chemicals through the micro-fluidic chip based on the charge and size of the respective molecules in the buffered aqueous solution;

f. contacting the buffered aqueous solution with an electrophoresis sensor to produce one or more chemical identification signals corresponding to the one or more chemical tracers present in the aqueous layer;

g. passing the one or more chemical identification signals produced by the electrophoresis sensor to an electronic data information collection system for indexing and storage in association a unique sample identification code;

h. comparing the chemical identification data from the aqueous layer to the relational database of chemical identification data prepared from chemical tracers used in the well completion and identifying any matches;

i. transmitting the data corresponding to the matches identified in step (h) to a communication system to produce conditioned data; and j. transmitting the conditioned data to display and/or printing means accessible to well management personnel.

2. The method of claim 1, wherein the transmission of the alarm signal from the water-cut sensor and the actuation of the automatic sampling valve is wireless.

3. The method of claim 1, wherein the aqueous layer is pressurized and passed to the micro-fluidic chip by a peristaltic pump.

4. The method of claim 1, wherein the potential difference applied in step (e) is in the range of from 1 kV to 5 kV volts.

5. The method of claim 1, wherein the conditioned data is compared to the relational database of known chemical tracers stored in a memory device associated with a microprocessor to identify any matches.

6. The method of claim 1, wherein the buffer is selected from the group consisting of acetic acid, boric acid, glycine, phosphoric acid, taurine, tricine and citric acid.

7. The method of claim 1, wherein control signals and data are transmitted to and from a supervisory control and data acquisition (SCADA) unit.

8. The method of claim 1, wherein a flushing buffer solution is introduced under pressure into conduits and vessels downstream of the automated sampling valve, including the micro-fluidic chip after completion of the electrophoresis analysis to remove all of the sample from the vessels and conduits in preparation for introduction of a new aqueous sample.

9. The method of claim 8, wherein the flushing step is automated and is initiated by a microprocessor controller.

10. A system for identifying one or more chemical tracers present in a produced hydrocarbon oil/water stream in a pipeline from a downhole well completion, the one or more chemical tracers, each having a predetermined chemical identification, having originally been applied to an outer surface of one or more lengths of tubing placed at known locations in the downhole well completion, the chemical identification of each of the chemical tracers and the location of each of the tracers having been retrievably recorded for the well completion in the form of a relational database, the system comprising:

a. a water-cut sensor for detecting water present in the oil/water stream flowing in the pipeline and an associated alarm for transmitting a signal to a central control station, and/or to a microprocessor controller;

b. an automated sampling valve in communication with the water-cut sensor alarm and in electronic communication with the central control station and/or the microprocessor controller, the automated sampling valve configured to open for a predetermined period of time in response to a signal to pass a predetermined volume of a sample from the produced oil/water stream through a sampling point in the pipeline;

c. a sample collection vessel in fluid communication with the automated sampling valve for receiving the sample of oil/water from step (b), the sample collection vessel comprising an outlet port proximate the bottom of the vessel for passage of a portion of an aqueous layer of the sample following settling; and d. a resilient polymeric sample transfer tube disposed to receive a portion of the settled aqueous sample, the transfer tube being in fluid communication with an inlet of a peristaltic pump, the peristaltic pump configured and controlled to transfer from an outlet port a predetermined volume of the aqueous layer under pressure to an electrophoresis analysis micro-fluidic chip, where the micro-fluidic chip comprises:
an inlet for admitting the aqueous sample,
an inlet for admitting a liquid buffer solution,
electrical connections for receiving a controlled voltage, and
an electrophoresis sensor;

e. a micro-fluidic chip electronic control and acquisition unit in electronic communication with the electrophoresis sensor;

f. an electronic data information collection unit in electronic communication with the micro-fluidic chip electronic control and acquisition unit;

g. signal communication means for transmitting conditioned data from the electronic data information collection unit to the central control station for comparison with, and identification of data associated with the chemical tracers and the location of the chemical tracers in the well completion from the relational database; and h. a user display device for displaying the results of the data comparison and identification of step (g).

11. The system of claim 10 which comprises an aqueous sample retention vessel having an inlet port in fluid communication with the outlet port of the sample collection vessel, and an outlet port in fluid communication via the resilient polymeric sample transfer tube with the peristaltic pump.

12. The system of claim 11 in which the aqueous sample retention vessel and the peristaltic pump are located in a protective housing.

13. The system of claim 12 in which the sample retention vessel comprises a valved waste discharge port in fluid communication with a waste storage vessel.

14. The system of claim 10 which includes a sensor for monitoring the pressure of the aqueous sample at the inlet of the micro-fluidic chip and transmits a signal to a controller operably connected to the peristaltic pump motor to maintain the pressure within a predetermined range by varying the speed of the peristaltic pump.

15. The system of claim 14 where the controller is the microprocessor controller.

16. The system of claim 14 which includes a variable pressure relief valve between the peristaltic pump and the inlet of the micro-fluidic chip which opens when the pressure of the aqueous sample exceeds a predetermined valve and closes when the pressure drops to a predetermined value.

17. The system of claim 16 in which the flushing buffer solution storage vessel comprises a low solution level sensor configured to transmit an alarm signal when the buffer solution reaches a predetermined level and to disable the automated sampling valve when a second lower predetermined solution level is reached.

18. The system of claim 10 which includes at least one storage battery operably connected to a voltage controller configured to supply a predetermined variable voltage to the micro-fluidic chip.

19. The system of claim 13 which includes a solar energy collection panel operably connected to the at least one storage battery.

20. The system of claim 19 which includes a recording and transmitting ampmeter/voltmeter operably connected to the storage battery and to a transmitter for transmitting data for monitoring the condition of the at least one battery.

21. The system of claim 10 which includes a signal transmitter and receiver operably connected to an antenna for transmitting to and receiving signals from a remote central control station.

22. The system of claim 10 which includes a flushing buffer solution storage vessel in fluid communication with a conduit downstream of the automated sampling valve.

\* \* \* \* \*